United States Patent [19]

Gleichner

[11] 4,231,715
[45] Nov. 4, 1980

[54] CLINICALLY USABLE PUMP APPARATUS FOR A DILATATION DEVICE

[75] Inventor: Hans Gleichner, Zurich, Switzerland

[73] Assignee: Schneider Medintag AG, Zurich, Switzerland

[21] Appl. No.: 853,189

[22] Filed: Nov. 21, 1977

[30] Foreign Application Priority Data

Oct. 21, 1977 [CH] Switzerland ............ 12834/77

[51] Int. Cl.³ .............. F05B 49/08; F04B 49/00; F04B 21/00
[52] U.S. Cl. .................. 417/307; 417/63; 128/218 A; 417/403
[58] Field of Search ............ 417/63, 307; 128/218 A, 128/DIG. 1, 1 D

[56] References Cited

U.S. PATENT DOCUMENTS

| | | | |
|---|---|---|---|
| 2,135,148 | 11/1938 | Roy | 417/63 |
| 2,786,468 | 3/1957 | Singer et al. | 128/218 A |
| 3,266,487 | 8/1966 | Watkins et al. | 128/1 D |
| 3,313,291 | 4/1967 | Marshall | 128/218 A |
| 3,331,538 | 7/1967 | Higgins | 128/218 A |
| 3,425,416 | 2/1969 | Loughry | 128/218 A |
| 3,426,744 | 2/1969 | Ball | 128/1 D |
| 3,515,130 | 6/1970 | Tsujino | 128/218 A |
| 3,605,745 | 9/1971 | Hodosh | 128/218 A |
| 3,612,722 | 10/1971 | Weward | 417/63 |
| 3,712,290 | 1/1973 | Irnish et al. | 128/1 D |
| 3,799,406 | 3/1974 | St. John et al. | 128/218 A |
| 4,104,008 | 8/1978 | Hoffmann | 417/401 |

FOREIGN PATENT DOCUMENTS

| | | | |
|---|---|---|---|
| 1548575 | 10/1968 | France | 128/218 A |
| 328065 | 4/1930 | United Kingdom | 417/63 |

*Primary Examiner*—William L. Freeh
*Attorney, Agent, or Firm*—Werner W. Kleeman

[57] ABSTRACT

A clinically usable pump apparatus for a dilatation device comprising a dilatation catheter, preferably for opening a stenosis and occlusions or for closing vessels, ducts and openings, while using a pumpable medium, which comprises a pump structured to accomplish the double function of producing positive pressure and negative pressure and operatively connected with the dilatation catheter.

2 Claims, 3 Drawing Figures

CLINICALLY USABLE PUMP APPARATUS FOR A DILATATION DEVICE

BACKGROUND OF THE INVENTION

The present invention relates to a new and improved construction of a clinically usable pump apparatus for a dilatation device having a dilatation catheter, preferably for opening stenoses and occlusions or for closing vessels, ducts and openings, while using a pumpable medium.

Based upon the work of Doctors Charles T. Dotter and Melvin P. Judkins (Transluminal Treatment of Arteriosclerotic Obstruction. Circulation 30, pages 654-670, 1964) there have been developed spherical-shaped, balloon-like dilatation catheters which can be positioned at the site of the stenosis and expanded by pressurized water supplied internally of the catheter. No pressure control is possible with this equipment. In order to pressure relieve the dilatation catheter a vent to the atmosphere is opened.

What is disadvantageous with this equipment is that the reduction in pressure, especially at the lower pressure region when approaching atmospheric pressure and due to the narrow flow paths, only can be accomplished extremely slowly and unsatisfactorily. As a result the dilatation catheter remains in a dilated state for a relatively long period of time, although it is exactly in medical applications that rational operation is extremely valuable. Venting into the atmosphere does not preclude air from reentering the dilatation catheter and when encountering unfavorable conditions such air possibly entering the bloodstream. Without any pressure control the momentarily attained dilatation cannot be predicted ahead of time and the danger exists of localized overloading at the treated site.

SUMMARY OF THE INVENTION

Hence, with the foregoing in mind it is a primary object of the present invention to provide a new and improved construction of a pump apparatus capable of use with a dilatation device which is not associated with the aforementioned drawbacks and limitations of the prior art proposals.

Another important object of the present invention aims at the construction of a new and improved pump apparatus enabling rapid filling and at least partial evacuation of the dilatation catheter and does not require any venting into the atmosphere.

Still, a further significant object of the present invention aims at the provision of a clinically usable pump apparatus for a dilatation device which enables carrying out a pressure control.

Now in order to implement these and still further objects of the invention, which will become more readily apparent as the description proceeds, the pump apparatus of this development contemplates a pump which is operatively connected with the dilatation catheter and such pump being structured for carrying out a double function of generating positive pressure as well as negative pressure. By means of the negative pressure a suction action is exerted at the inner space of the dilitation catheter, so that such is evacuated.

It is advantageous if the dilitation catheter is directly connected with the pump, in other words, the medium conveyed by the pump simultaneously serves as the work medium for the catheter, because in this way there is obtained a much simpler construction.

An advantageous further variant design of the inventive apparatus is realized by providing a measuring device for checking the generated positive pressure and negative pressure, respectively. In this way there can be controlled as a function of time the pressure changes during the operation of the equipment and there can be avoided any too rapid fluctuations.

An analogous modification also can be realized by providing an excess-pressure or pressure relief valve to prevent exceeding a preselected maximum pressure in the dilatation catheter. By providing such pressure limiting action there are eliminated the effects of any possible operating errors.

For the field of use under consideration there is particularly suitable a piston pump which is constructed to possess a reciprocating piston which is effective in both of its translatory directions. For this purpose, namely the double function of the piston for generating both positive pressure and negative pressure, it is advantageous if the piston pump has two sealing rings.

A reliable sealing action is realized if each sealing ring consists of an O-ring mounted in a peripheral groove of the pump piston and a lip ring located thereover. Due to this divided construction of the sealing ring the inwardly situated O-ring performs the necessary spring or cushioning action and the lip ring serves for sealing purposes, something extremely favorable with regard to service life.

Advantageously, the pump is not manually operated, rather by a mechanical device. Human shortcomings thus can be at least partially eliminated.

According to a preferred construction the mechanical drive device essentially comprises a cylinder with a work piston which is impinged at both faces by a pressurized medium. Due to the similar mode of operating the work and pump pistons it is thus best possible to coordinate their coaction.

It is of advantage to employ for the drive of the work or working piston a gaseous pressurized medium. By virtue of the compressibility of the gas there is realized a soft actuation of the pump piston and thus the entire apparatus.

A pressure reducing valve in the flow path of the pressurized medium affords the possibility of downwardly throttling the pressure of the medium which flows to the drive device, and thus, facilitating a careful actuation of the apparatus.

A further construction of the equipment resides in arranging a respective pressure reducing valve in both infeed lines to the cylinder of the drive device in order to obtain different velocities for the forward and return movement of the work piston. In this way there can be, for instance, realized the result that within the pump cylinder the positive pressure is only generated with a delayed or retarded action, the negative pressure however more rapidly.

It has been found to be advantageous to separate the pump from the mechanical drive device, something which is then especially beneficial when work should be carried out as sterile as possible at the pump or at the dilatation catheter.

An advantageous construction of the apparatus contemplates arranging in alignment and coupling with one another a piston rod of the pump and a piston rod of the mechanical drive device. Due to such direct transmission of the movement of the work piston to the pump piston there is realized a simple arrangement, which, additionally, only produces low frictional forces.

In order to achieve a particularly rapid disconnection of the pump from the mechanical drive device, it is advantageous to arrange at the piston rod a coupling body or element having a dovetail-shaped groove into which there can be inserted a fitting member corresponding to the cross-section of the groove and secured to the other piston rod.

BRIEF DESCRIPTION OF THE DRAWING

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
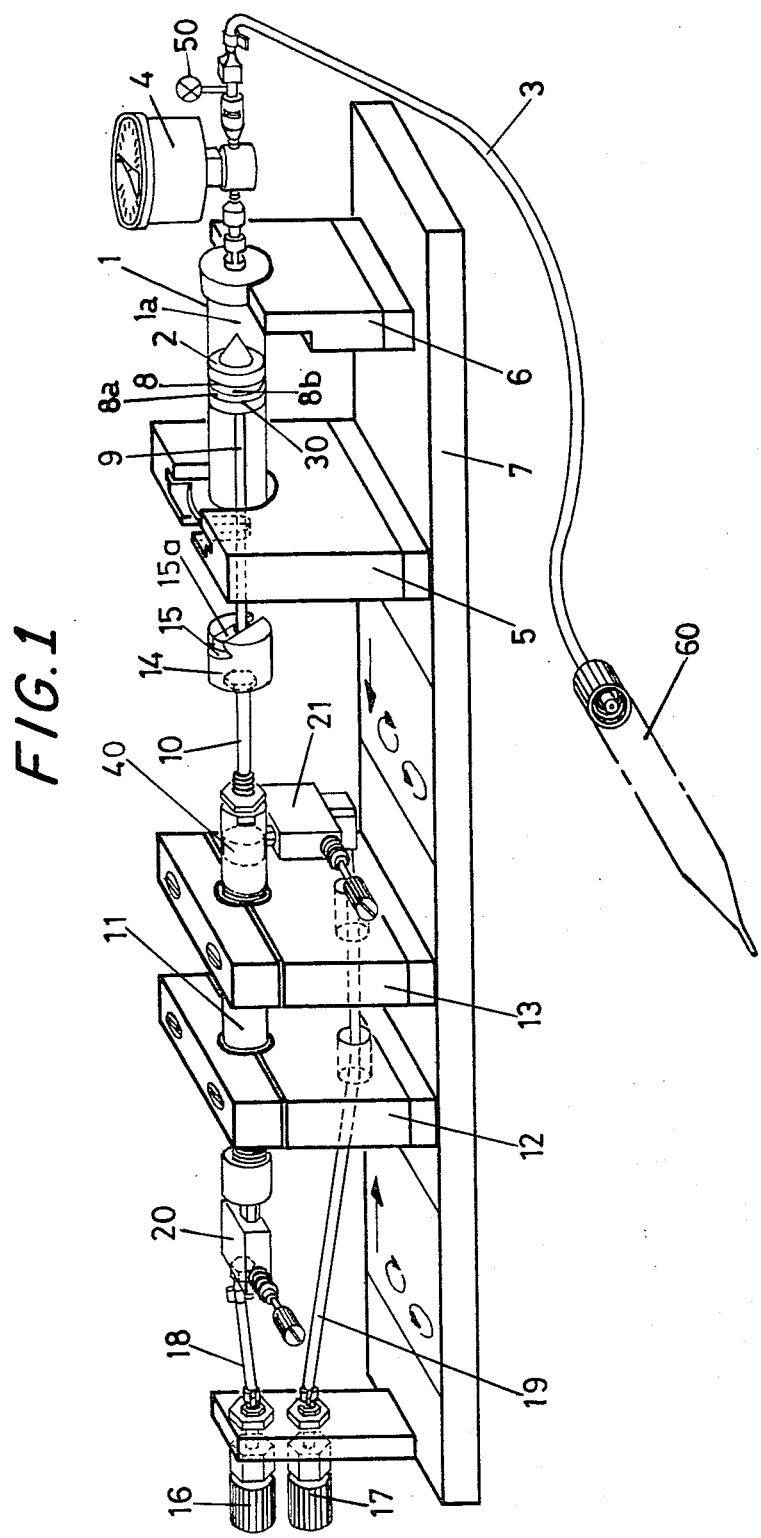
FIG. 1 schematically illustrates a preferred exemplary embodiment of a clinically usable pump apparatus for a dilatation device.

Describing now the drawings and particularly FIG. 1, the pump apparatus comprises a pump essentially composed of a cylinder 1 and a pump piston 2 which is slidingly arranged in cylinder 1. The cylinder compartment 1a located to the right of the piston 2 is filled with a pumpable medium, as is also the connection line or conduit 3 which leads to a mere schematically illustrated dilatation catheter, generally indicated by reference character 60, which may be of the type disclosed in the commonly assigned United States application, Ser. No. 853,190, filed Nov. 21, 1977 now U.S. Pat. No. 4,019,563 entitled "Catheter Arrangement, Method Of Catheterization, And Method Of Manufacturing A Dilatation Element", to which reference may be readily had and the disclosure of which is incorporated herein by reference.

Now between the cylinder 1 and the connection line or conduit 3 there is arranged a pressure measuring device 4 which may be for instance a manometer. Instead of the pressure measuring device 4, or in addition thereto, there also can be provided a standard excess-pressure valve or pressure relief valve, as indicated by reference character 50. The cylinder 1 is inserted into support plates 5 and 6 and there is not required any special attachment. The support plates 5 and 6 are secured to a base plate 7.

The pump piston 2 is provided with two sealing rings 8 for the purpose of sealing the same within the pump cylinder 1. Each of the sealing rings 8 comprises an O-ring 8a mounted in a peripheral groove 30 of the piston 2 and a lip ring lying over the O-ring 8a, this lip ring having only been partially shown in the drawing to reveal the O-ring and has been conveniently designated by reference character 8b.

The piston rod 9 of the piston 2 is coupled with the therewith aligned piston rod 10 which belongs to a mechanical drive device. The mechanical drive device essentially consists of the cylinder 11 and the work or working piston 40 which has been schematically shown in broken or phantom lines and pressure impinged at both faces thereof. The work piston 40 is slidably arranged within the cylinder 11 and such cylinder 11 is mounted in the support plates 12 and 13.

At the piston rod 10 there is arranged the coupling element or body 14 which has a dovetail-shaped groove 15. Into the dovetail groove 15 there is inserted a fitting element 15a, only part of which is shown, and which is complementary in cross-sectional shape to the shape of groove 15 and secured to the piston rod 9.

The connection elements 16 and 17 communicate by means of the infeed lines or conduits 18 and 19, respectively, with both ends of the cylinder 11 and thus with opposite faces of the work piston 40. A respective pressure reducing valve 20 and 21 is incorporated into the infeed lines 18 and 19 respectively.

Having now had the benefit of the foregoing discussion the mode of operation of the pump apparatus will be considered and is as follows:

By means of the connection element 16 and the infeed line 18 a pressurized medium is delivered to the cylinder 11. In principle there can be employed most every liquid or gaseous medium, but a compressible medium allows for a more subtle operation of the equipment. The pressurized medium moves the work piston 40, and thus, by means of the coupled piston rods 10, 9 the pump piston 2 to the right of the showing of the drawing of FIG. 1. The medium located in the cylinder 1 is pressed into the connection line or conduit 3 and fills the dilatation catheter 60 which is connected therewith. The generated pressure is monitored at the pressure measuring device 4. As soon as the desired pressure has been reached then there is interrupted the infeed of the pressurized medium to the connection element 16, and the entire apparatus assumes its rest or static condition. If there is provided the excess pressure valve 50, then a predetermined pressure cannot be exceeded. The selection of a maximum pressure of 3 to 8 atmospheres excess pressure has been found to be advantageous.

Also the medium conveyed by the pump in principle can be liquid or gaseous. For clinical use it is however too dangerous to use a compressible medium. For the purposes herein described by way of example there has been found to be suitable a mixture of a physiological sodium chloride solution and an x-ray contrast agent.

For relieving the pressure and evacuation of the dilatation catheter 60 the pressurized medium is delivered by means of the connection element 17 and the infeed line 19 to the other side of the cylinder 11. As a result, the work piston 40, the piston rods 9, 10 and the pump piston 2 move towards the left of the showing of the drawing of FIG. 1, in the pump there prevails a negative pressure and the medium is sucked-out of the catheter.

With this equipment it is possible to produce different velocities of the pistons in both directions. If, for instance, the pressure reducing valve 20 is more intensely throttled than the valve 21, then the movement of the piston 40 towards the right is accomplished more slowly than towards the left, enabling a careful, well controlled pressure buildup in the dilatation catheter.

If the velocity in both translatory directions can be of the same magnitude, then it is sufficient to have a single pressure reducing valve in the common infeed line for the pressurized medium before it is delivered to both connection elements 16 and 17.

Figure 2:
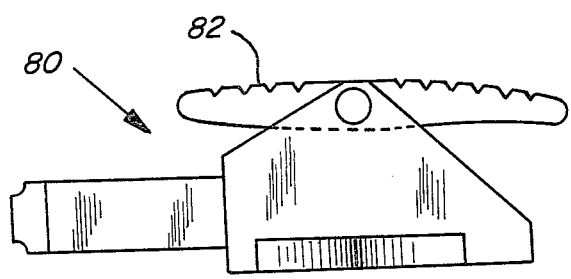
FIG. 2 is a schematic side view of a foot-operated tiltable or rocker-type switch which can be used with the arrangement of FIG. 1.
Figure 3:
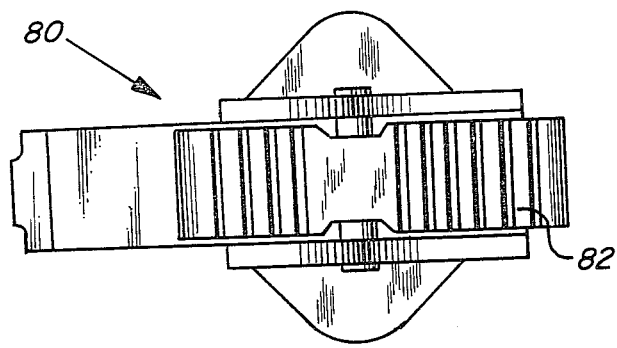
FIG. 3 is a top plan view of the tiltable switch of FIG. 2.

The apparatus can be actuated in a simple manner with the foot of the user by providing a rocker-type or tiltable switch 80 as shown in FIGS. 2 and 3. Movement of the switch i.e., the foot-operated pedal 82 in the one direction causes the pressurized medium to be delivered to the left side of the cylinder 11 and pressure is produced in the pump. Movement of the switch pedal 82 in the other direction causes the pressurized medium to be delivered to the right side of the cylinder 11 and a negative pressure prevails in the pump. Upon release of the switch the equipment remains at standstill.

The described construction of coupling enables the pump to be pushed out upwardly, and the fitting element 15a slides out of the groove 15 in the coupling body 14. For coupling purposes the fitting element 15a is again inserted into the coupling body 14 and the pump is placed upon the support plates 5 and 6. No further attachment is required. The possibility of disconnecting the pump from the mechanical drive device is especially advantageous during the hereinafter discussed gas sterilization.

For the drive of the pump there can be employed any useful mechanical device. In an operating room there is however not desired any vibration whatsoever, as such would be unavoidable for instance when using a motor drive. The use of a pressurized medium is therefore preferred.

The pump as well as the pressure measuring device, connection lines and dilatation catheter are advantageously prepared for clinical use by carrying out a conventional gas sterilization so that also in the case of damage to the catheter germs cannot enter the human body.

While there are shown and described present preferred embodiments of the invention, it is to be distinctly understood that the invention is not limited thereto, but may be otherwise variously embodied and practiced within the scope of the following claims.

Accordingly, what I claim is:

1. A clinically usable pump apparatus for a dilatation device having a dilatation catheter, preferably for opening stenoses and occlusions or for closing vessels, ducts and openings, while utilizing a pumpable medium, comprising:
   a pump adapted to be connected with the dilatation catheter for applying controlled positive pressure and negative pressure conditions to the dilatation catheter;
   means for structuring the pump for accomplishing the double function of generating a positive pressure as well as a negative pressure in a closed hydraulic system between the pump and the dilatation catheter;
   mechanical drive means for driving said pump;
   said mechanical drive means comprises:
      a work cylinder;
      a work piston slidably arranged in said cylinder for carrying out forward and return strokes;
      said work piston having opposite faces;
   means for supplying and impinging opposite faces of said work piston with a pressurized medium; and
   an excess-pressure valve for preventing that a preselected maximum pressure will be exceeded in the dilatation catheter.

2. A clinically usable pump apparatus for a dilatation device having a dilatation catheter, preferably for opening stenoses and occlusions or for closing vessels, ducts and openings, while utilizing a pumpable medium, comprising:
   a pump adapted to be connected with the dilatation catheter for applying controlled positive pressure and negative pressure conditions to the dilatation catheter;
   means for structuring the pump for accomplishing the double function of generating a positive pressure as well as a negative pressure in a closed hydraulic system between the pump and the dilatation catheter;
   mechanical drive means for driving said pump;
   said mechanical drive means comprises:
      a work cylinder;
      a work piston slidably arranged in said cylinder for carrying out forward and return strokes;
      said work piston having opposite faces;
   means for supplying and impinging opposite faces of said work piston with a pressurized medium;
   said pump comprising a piston pump having a piston rod;
   said mechanical drive means further including a piston rod provided for the work piston;
   said piston rod of the pump and said piston rod of said mechanical drive means being arranged essentially in alignment with one another;
   means for operatively coupling said piston rod of said pump and said piston rod of said mechanical drive means with one another; and
   said coupling means comprising a coupling body having a substantially dovetail-shaped groove provided at one of the piston rods and a fitting element having a cross-section corresponding essentially to said groove attached to the other piston rod.

* * * * *